United States Patent [19]

Cregge et al.

[11] Patent Number: 4,578,464
[45] Date of Patent: Mar. 25, 1986

[54] 6-HYDROXYALKYLAMINO-8-METHYL-1,2,4-TRIAZOLO-[4,3-B]PYRIDAZINE AND RELATED COMPOUNDS

[75] Inventors: Robert J. Cregge, Zionsville, Ind.; John E. Coutant, Loveland, Ohio

[73] Assignee: Merrell Dow Pharmaceuticals Inc., Cincinnati, Ohio

[21] Appl. No.: 554,475

[22] Filed: Nov. 22, 1983

[51] Int. Cl.$^4$ .................... C07D 487/04; A61K 31/41
[52] U.S. Cl. .................................................. 544/236
[58] Field of Search ......................................... 544/236

[56] References Cited

U.S. PATENT DOCUMENTS 3,915,968 10/1975 Bellasio et al. .................... 260/247.5
4,136,182 1/1979 Lewis et al. ...................... 424/248.54

FOREIGN PATENT DOCUMENTS 29130 5/1981 European Pat. Off. ............ 544/234

OTHER PUBLICATIONS

Kosary et al., Heterocycles, vol. 20 (5) 1983, pp. 749–752.

Primary Examiner—Mark L. Berch
Assistant Examiner—William A. Teoli, Jr.
Attorney, Agent, or Firm—John J. Kolano

[57] ABSTRACT

8-Methyl-1,2,4-triazolo[4,3-b]pyridazines having a hydroxyalkylamino substituent at the 6-position are described herein. The compounds involved are useful as bronchodilator agents and they are prepared by the reaction of 6-chloro-8-methyl-1,2,4-triazolo[4,3-b]-pyridazine with an appropriate amino alcohol.

7 Claims, No Drawings

6-HYDROXYALKYLAMINO-8-METHYL-1,2,4-TRIAZOLO-[4,3-B]PYRIDAZINE AND RELATED COMPOUNDS

The present invention is directed to 6-hydroxyalkylamino-8-methyl-1,2,4-triazolo[4,3-b]pyridazines having the following general formula

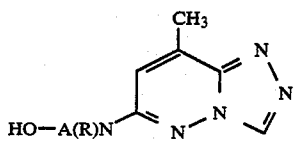

wherein A and R are selected so that A represents straight-chain alkylene of 2-5 carbon atoms and R represents hydrogen; or the two groups are combined so that HO—A(R)N— represents hydroxy- 1-piperidinyl.

A preferred group of compounds are those wherein A is a straight-chained alkylene group of 2-5 carbon atoms. Examples of such alkylene groups are ethylene, trimethylene, tetramethylene and pentamethylene with ethylene and trimethylene being particularly preferred groups.

When the 6-amino substituent in the compounds of the present invention is a piperidino group, that group contains a hydroxy substituent which can be located at any available position on the ring.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicyclic, 4-aminosalicyclic, 2-phenoxybenzoic, 2-acetoxybenzoic, mandelic and like acids; and with organic sulfonic acids such as methanesulfonic acid and p-toluenesulfonic acid.

To prepare the compounds of the present invention, a 6-halo-8-methyl-1,2,4-triazolo[4,3-b]pyridazine, wherein the halo is chloro or bromo, is reacted with an amine of the formula:

HO—A(R)NH wherein A and R are defined as above. The indicated reactants are heated together to give the desired compounds. An excess of the amine is conveniently used as a solvent for the reaction although it would be possible to use common organic solvents as long as they dissolved the reactants and they were inert with respect to the reactants. An example of one such alternative solvent would be 2-propanol. When the reaction is carried out in an inert solvent, an excess of amine would still be useful although not a large excess as when the amine serves as the solvent. Hydrogen halide is formed in the reaction and it reacts with free amine present so that excess amine is used to allow for this reaction. Alternatively, it would be possible to use a tertiary amine, such as triethylamine, to react with the hydrogen chloride formed in the reaction.

In order to obtain the halide starting material referred to above, citraconic anhydride is reacted with hydrazine to give the corresponding (cyclic) hydrazide. This hydrazide is then reacted with phosphorus oxychloride to give 3,6-dichloro-4-methylpyridazine. The bromo compound could be obtained in a similar manner. The di-halo compound is then reacted with hydrazine to replace one of the halogen atoms and give a mixture of two hydrazino pyridazines. The mixture of isomers can be separated by treatment with ethanol to give the desired 6-chloro-3-hydrazino-4-methylpyridazine. Reaction of this compound with formic acid brings about cyclization to give the 1,2,4-triazolo[4,3-b]pyridazine ring structure and the appropriate starting material referred to originally.

The substituted 6-hydroxyalkylamino-8-methyl-1,2,4-triazolo[4,3-b]pyridazine compounds as described above are bronchodilators and are thus useful for the treatment of bronchial disorders such as bronchial asthma. The present invention is further directed to a method of effecting bronchodilation.

In practicing the method of this invention, an effective bronchodilating amount of 1 or more substituted 6-hydroxyalkylamino-8-methyl-1,2,4-triazolo[4,3-b]pyridazines of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 5 to about 500 milligrams of substituted 6-hydroxyalkylamino-8-methyl-1,2,4-triazolo[4,3-b]pyridazine compound per kilogram of animal body weight with other ranges being from about 5 to about 50 or from 5 to about 15 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired.

In practicing the method of this invention, the active ingredient is preferably incorporated in a composition comprising a pharmaceutical carrier and from about 5 to about 90 percent by weight of the substituted 6-hydroxyalkylamino-8-methyl-1,2,4-triazolo[4,3- b]pyridazine compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Penn.

Evidence of the bronchodilator activity of the present compounds can be obtained from in vitro testing of isolated segments of male guinea pig trachea. This is suspended in a modified Burn solution, aerated with 95% oxygen and 5% carbon dioxide and placed under a tension of 8 g. Tissues were precontracted with one of several contractile agents histamine($1 \times 10^{-5}$M), 5-hydroxytryptamine ($2 \times 10^{-6}$M) or potassium chloride (20 mM)]at a concentration that produced 70-80% of its maximal response, previously determined from concentration-contraction curves. Test compounds were then added to the baths in a cumulative manner until maximal relaxation responses were obtained. The relaxant effect of each concentration of test compound was expressed as a percentage of that obtained with $3.2 \times 10^{-7}$M isoproterenol and these percentages were used to calculate the $ED_{50}$ of the test compound. All data points consisted of at least five different tissues. Two compounds known to have bronchodilator activity (aminophylline and 6-(1-piperidinyl)8-methyl,-1,2,4-triazolo[4,3-b]pyridazine) were tested at the same time for comparison purposes. The compounds of the present invention were found to reverse the contraction produced by the contractile agents, with an activity about ten percent of the comparison compounds.

In addition, in evaluating bronchodilator activity, test compounds were administered to guinea pigs by intraperitoneal injection or orally and the guinea pigs were challenged by exposure to a histamine aerosol at periods ranging from 30 minutes to 4 hours later. Untreated animals collapsed when exposed to the histamine aerosol. In the operations, the animals were observed and collapse times were recorded. The collapse times observed were then compared statistically with control animals treated with water alone. When tested by the above procedure, 6-(2-hydroxyethylamino)-8-methyl-1,2,4-triazolo4,3-b]pyridazine and 6-(3-hydroxypropylamino)-8-methyl-1,2,4-triazolo[4,3-b]pyridazine were found to produce a bronchodilating effect at a dose of about 30% (intraperitoneal) and 6-(4-hydroxy-1-piperidino-8-methyl-1,2,4-triazolo[4,3-b]pyridazine produced a bronchodilating effect at a dose of about 50% (oral) of their $LD_{50}$'s. These results, combined with the in vitro results described earlier, show that the present compounds are bronchodilators and not simply antihistamines.

The following examples are presented to illustrate the present invention but they should not be construed as limiting it in any way.

EXAMPLE 1

To a solution of 210 g of hydrazine dihydrochloride in 2 liters of water there was added, in one portion, 224 g of citraconic anhydride. When the mixture was heated to boiling with stirring, a homogeneous solution was first obtained and then a white precipitate started to form in the mixture. After 30 minutes at reflux, the mixture was allowed to cool with stirring. It was then cooled to 10° C. and the solid was separated by filtration and dried in a vacuum oven overnight to give citraconic hydrazide melting at about 281-283.5° C. with decomposition.

EXAMPLE 2

A suspension of 223 g of citraconic hydrazide in 1 liter of acetonitrile was prepared and 595 g of phosphorus oxychloride was added at room temperature. The resulting mixture was then slowly warmed to reflux with stirring. After 4 hours of reflux, the resulting hot dark-purple solution was poured into 3 liters of water with stirring. This solution was then further diluted with water to a total volume of 6 liters and then cooled. White needles formed and these were separated by filtration and air-dried to give 3,6-dichloro-4-methylpyridazine melting at about 86-87.5° C. A second crop of this product can be obtained by making the filtrate basic with aqueous 50% sodium hydroxide solution, separating the dark crystals obtained, and then percolating a methylene chloride solution of the solid through silica gel.

EXAMPLE 3

Hydrazine (500 ml) was added to 280 ml of water and the resulting hot hydrazine hydrate was poured onto 206 g of solid 3,6-dichloro-4-methylpyridazine. The mixture was then heated with stirring, and, after 10 minutes, a vigorous exotherm occurred and an almost complete solution of material was obtained. This mixture was heated at reflux for an additional 30 minutes and about 2.2 liters of water was added to give a clear solution. Analysis of the solution by reverse phase, high pressure, liquid chromatography showed that it contained a 60:40 ratio of 3-chloro-6-hydrazino-4-methylpyridazine and 6-chloro-3-hydrazino-4-methylpyridazine. The mixture was then cooled to below 20° C with stirring and the resulting thick suspension was filtered. The crystals obtained were washed with ice water, dried overnight under nitrogen, and then boiled in 1 liter of ethanol (to dissolve the undesired isomer). while the mixture was still warm, the supernatant liquid was decanted (about 500 ml) and 500 ml of fresh ethanol was added to the remaining solid suspension. The mixture was then heated again and supernatant liquid was again decanted (about 800 ml). Ethanol was again added to the residual suspension to give a total volume of 1.6 liters and this was again heated to reflux. Complete solution did not take place but the mixture was allowed to cool to 20° C and it was then filtered. The white crystals obtained in this was were washed with fresh ethanol and then with diethyl ether and air dried to give 6-chloro-3-hydrazino-4-methylpyridazine melting at about 191-192° C with decomposition. Analysis of the solid by high pressure, liquid chromatography showed that it was more than 97% pure compound.

EXAMPLE 4

A mixture of 37.6 g of 6-chloro-3-hydrazino-4-methylpyridazine and 50 ml of formic acid was heated, with stirring, on a boiling water bath for 30 minutes. The mixture was cooled and excess acid was removed by distillation under reduced pressure. The residual damp solid was dissolved in 300 ml of methylene chloride and washed with aqueous saturated sodium bicarbonate solution. The organic solution was then dried over anhydrous sodium sulfate and filtered through Celite and the solvent was evaporated to leave a residual tan solid. This was recrystallized from ethyl acetate to give 6-chloro-8-methyl-1,2,4-triazolo[4,3-b]pyridazine melting at about 134–136° C.

EXAMPLE 5

A mixture of 1 g of 6-chloro-8-methyl-1,2,4-triazolo[4,3-b]pyridazine and 3 g of 3-hydroxypiperidine was heated on an oil bath at 100° C. for 15 minutes. During this time, the solids melted to give a homogeneous mixture and analysis of the mixture by thin-layer chromatography showed that the reaction was complete. The mixture was then cooled and excess amine was removed by bulb-to-bulb vacuum distillation. The solid residue was then purified by percolation through silica gel (50 g) with a 90:10:1 solvent system of methylene chloride:ethanol:ammonium hydroxide. The resulting solid was then crystallized from a mixture of 2-propanol/hexane (1:6) to give 6-(3-hydroxy-1-piperidino)-8-methyl-1,2,4-triazolo[4,3-b]pyridazine melting at about 199–200° C. This compound has the following structural formula:

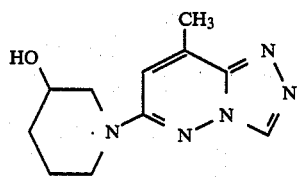

EXAMPLE 6

The procedure of Example 5 was repeated using 6-chloro-8-methyl-1,2,4-triazolo[4,3-b]pyridazine and other appropriate amino alcohols. In each case, the crude produce obtained was recrystallized from acetonitrile to give the following compounds:
6-(2-Hydroxyethylamino)-8-methyl-1,2,4-triazolo[4,3-b]pyridazine melting at about 205–206° C.
6-(3-Hydroxypropylamino)-8-methyl-1,2,4-triazolo[4,3-b]pyridazine melting at about 169–170° C.
6-(4-Hydroxybutylamino)-8-methyl-1,2,4-triazolo4,3-b]pyridazine melting at about 125–126° C.
6-(5-Hydroxypentylamino)-8-methyl-1,2,4-triazolo[4,3-b]pyridazine melting at about 136–137° C.
6-(4-Hydroxy-1-piperidino)-8-methyl-1,2,4-triazolo[4,3-b]pyridazine melting at about 182.5–183.5° C.

What is claimed is:

1. A compound of the formula

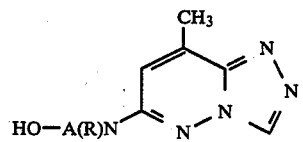

wherein A and R are selected so that A represents a straight-chain alkylene of 2–5 carbon atoms and R represents hydrogen; or the two groups are combined so that HO-A(R)N- represents hydroxy-1-piperdinyl.

2. A compound according to claim 1 which has the formula

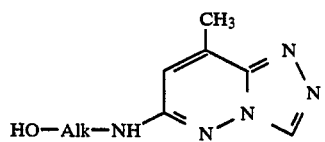

wherein Alk is a straight-chain alkylene containing 2–5 carbon atoms.

3. A compound according to claim 1 which is 6-(2-hydroxyethylamino)-8-methyl-1,2,4-triazolo[4,3-b]pyridazine.

4. A compound according to claim 1 which is 6-(3-hydroxypropylamino)-8-methyl-1,2,4-triazolo[4,3-b]pyridazine.

5. A compound according to claim 1 which has the formula

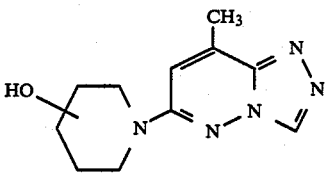

6. A compound according to claim 1 which is 6-(3-hydroxypiperidino)-8-methyl-1,2,4-triazolo[4,3-b]pyridazine.

7. A compound according to claim 1 which is 6-(4-hydroxypiperidino)-8-methyl-1,2,4-triazolo[4,3-b]pyridazine.

* * * * *